United States Patent [19]

Tavlarides et al.

[11] Patent Number: 5,074,658
[45] Date of Patent: Dec. 24, 1991

[54] LASER CAPILLARY SPECTROPHOTOMETRIC ACQUISITION OF BIVARIATE DROP SIZE AND CONCENTRATION DATA FOR LIQUID-LIQUID DISPERSION

[75] Inventors: Lawrence L. Tavlarides, Fayetteville, N.Y.; Jae-Heum Bae, Daejeon, Rep. of Korea

[73] Assignee: Syracuse University, Syracuse, N.Y.

[21] Appl. No.: 386,602

[22] Filed: Jul. 31, 1989

[51] Int. Cl.$^5$ .................. G01P 5/20; G01B 11/00; G01N 21/59
[52] U.S. Cl. ........................... 356/73; 356/27; 356/379; 356/436
[58] Field of Search ................. 356/70, 73, 379, 380, 356/440, 436, 432, 411, 27; 73/61.1 R, 55; 250/575, 577

[56] References Cited

U.S. PATENT DOCUMENTS

| | | | |
|---|---|---|---|
| 3,422,667 | 1/1969 | Hrdina | 73/61.1 R |
| 3,480,369 | 11/1969 | Smythe et al. | 356/440 |
| 3,556,659 | 1/1971 | Hawes | |
| 3,909,136 | 9/1975 | Thomas | 356/410 |
| 4,110,043 | 8/1978 | Eisert | |
| 4,205,973 | 6/1980 | Ryan | 356/380 |
| 4,366,384 | 12/1982 | Jensen | 250/575 |
| 4,585,344 | 4/1986 | Webster | |
| 4,605,305 | 8/1986 | Lenoir et al. | |
| 4,728,190 | 3/1988 | Knollenberg | |

FOREIGN PATENT DOCUMENTS 1342444 1/1974 United Kingdom ............. 250/577

OTHER PUBLICATIONS

*Ind. Eng. Chem., Fundam.,* "Breakage and Coalescence Processes in an Agitated Dispersion, Experimental System and Data Reduction", vol. 16, No. 3, 1977.
*Chem. Eng. Technol.,* "A New Method for the Prediction of Liquid Pulsed Sieve Tray Extractors", 10(1987), 73-86.

Primary Examiner—Richard A. Rosenberger
Attorney, Agent, or Firm—Wall and Roehrig

[57] ABSTRACT

A laser capillary spectrophotometric technique measures real time or near real time bivariate drop size and concentration distribution for a reactive liquid-liquid dispersion system. The dispersion is drawn into a precision-bore glass capillary and an appropriate light source is used to distinguish the aqueous phase from slugs of the organic phase at two points along the capillary whose separation is precisely known. The suction velocity is measured, as is the length of each slug from which the drop free diameter is calculated. For each drop, the absorptivity at a given wavelength is related to the molar concentration of a solute of interest, and the concentration of given drops of the organic phase is derived from pulse heights of the detected light. This technique permits on-line monitoring and control of liquid-liquid dispersion processes.

12 Claims, 10 Drawing Sheets

LASER CAPILLARY SPECTROPHOTOMETRIC ACQUISITION OF BIVARIATE DROP SIZE AND CONCENTRATION DATA FOR LIQUID-LIQUID DISPERSION

This invention was made with the United States Government's support under Grant No. DE-AC02-82ER13002 awarded by the Department of Energy. The United States Goverment has certain rights in the invention under this grant.

BACKGROUND OF THE INVENTION

The present invention relates to apparatus and technique for counting, measuring, and classifying liquid droplets, and is more especially directed to a technique for measuring drop size and concentration for droplets in a liquid-liquid dispersion. The invention is concerned with a laser capillary technique for near real-time measurement of bivariate drop size and concentration distribution and of monovariate drop size distribution or monovariate concentration distribution.

Contact of two immiscible liquids with one another typically involves mass transfer across a boundary between the liquids. This can occur with or without accompanying chemical reaction, and often involves liquids in stirred tanks, typical of petrochemical, hydrometallurgical, food, pharmaceutical, and polymer industries. Intimate contact is established between two liquid streams to ensure adequate rates of interphase mass transfer and or chemical reaction. This intimate contact is usually promoted by dispersing one phase as droplets in a second, continuous phase.

Many investigators have reported that the dispersed phase mixing can have a significant effect on the reactor performance. Further, theoretical work is at hand to model the effects of droplet mixing on conversion and selectivity for liquid-liquid dispersions. However, no experimental technique which can measure bivariate drop size - concentration distribution for reactive liquid-liquid dispersions has been proposed.

A variety of experimental approaches have been used to measure interfacial areas and drop size distributions in a liquid-liquid dispersions. The most common method is still the direct photography method. This method is simple, easy and accurate, but it cannot be used for high holdup fraction, especially in the case of optically dark liquid dispersion systems. The procedure usually requires many pictures and lengthy time for analysis. Direct image analysis of the data has met with only limited success for dilute dispersions.

The light transmission technique has been widely used in determining the interfacial area (or so-called Sauter mean diameter) in liquid-liquid dispersions. The method is simple and has the advantages of quick measurement and on-line operation. However, only interfacial area can be measured by this method.

The light-scattering method has been used for measurement of small drop sizes in the range below 10 $\mu$m diameter, and more recently, measurement of larger drop sizes (below 800 $\mu$m in diameter). Although continuous sampling is possible, the technique is limited to low dispersed phase holdup fraction (below 0.05).

The Laser Doppler Velocimetry (LDV) technique uses the doppler effect (frequency shift information) and light scattering by particles to determine drop size and drop velocity. The feasibility of the technique has been demonstrated for measurement of broad ranges of drop sizes in solid-liquid (sol) and liquid spray (aerosol) systems. However, for liquid-liquid systems there are significant limitations, especially at high dispersed phase fraction.

Drop size distribution may be obtained by using a Coulter Counter for directly observing drops suspended in an electrically conductive continuous phase. The dispersion is forced through a small aperture between two electrodes. By changing the aperture distance, a broad drop size distribution can be obtained. In this technique, however, the counting of particles necessitates the addition of undesirable conductive materials to the dispersion. The addition of these materials can affect the drop diameter and the breakup and coalescence rates in the dispersion. Furthermore, these effects are unpredictable.

The use of chemical means to measure the interfacial area has been used extensively for gas-liquid dispersions. Chemical reaction methods for determining the interfacial area of liquid-liquid dispersions requires a reactant of relatively unchanging dispersed phase concentration, which diffuses to the continuous phase. The effective interfacial area can be obtained from the extraction rate and physico-chemical properties of the system. The disadvantage of this method is the effect of the mass transfer on the physico-chemical properties of the dispersion. It has been observed that mass transfer can affect the interfacial tension and thus interfacial area.

Drop stabilization methods rely on the immediate stabilization of drops by encapsulation with thin polymer films or surfactants. A photomicrographic method has usually been employed after encapsulation of drops in the application of this technique. However, the drop stabilization method cannot be used for some liquid-liquid dispersion systems due to incompatability of encapsulating materials for those systems. This method also has disadvantages of influence of the chemical treatment on drop size. According to Verhoff et al., Breakage and Coalescence Processes in an Agitated Dispersion, *Experimental System and Data Reduction*, 16 *Ind. Eng. Chem. Fundam.* 371 (1977), a special sampling apparatus was used to withdraw a sample of dispersed phase from a mixing vessel, to stabilize drops with a surfactant, and to force the dispersed sample through a capillary with a photometer assembly to measure both size and dye concentrations of drops. This technique was applied to the system of a non-transferring, non-surface-active and non-reactive dye present only in the dispersed phase for the mixing experiments.

A capillary method employs a fine-bore capillary of the same order as the droplet sizes for sampling from the liquid dispersion in the vessel. This method can be used for obtaining broad drop size distribution in the range above 0.05 mm in diameter, at real time and automatically. One such capillary sampling system measured drop sizes in the range 0.05 to 0.6 mm for a heptane-water system in a batch reactor using a capillary of 0.2 mm in diameter. Another technique employed several different sizes of capillaries for measurement of monodispersed drops of butyl acetate in water, the drops being in the range of 2 mm to 5 mm in diameter. According to Pietzsch and Blass, A New Method For the Prediction of Liquid Pulsed Sieve-Tray Extractors, 10 *Chem. Eng. Technol.* 73–86 (1987), this capillary sampling method can be adapted to measure drop sizes for toluene-water and tributyl phosphate-n-alkane/water systems in a pulsed sieve-tray extraction column.

Average drop size and volume fraction of the dispersed phase in liquid-liquid systems can be measured by the acoustic wave method. The principle of that method is based on the difference between the transmission velocities of acoustic waves in the two liquids. This technique can measure, at real time, but has limitations to measure small drop sizes (below 1000 μm).

The scintillation method uses short range radioactive particles for measuring interfacial area for liquid dispersion systems. However, this technique is limited by the need for high immiscibility between phases, and is further limited by the availability of suitable isotopes and target materials.

Only the technique of Verhoff et al., mentioned above, could measure bivariate size and concentration distribution of drops, although that possibility is limited to a non-reacting and non-mass transfer tracer system. The capabilities of existing capillary measurement techniques are rather limited, and do not give realistic size and concentration data in real time.

OBJECTS AND SUMMARY OF THE INVENTION

It is an object of the present invention to provide a technique for simultaneous measurement of drop size and drop concentration distribution in real time, and in situ and which avoids the drawbacks of the prior art.

It is another object to provide a technique to produce bivariate drop size and drop concentration data which can be analyzed on line.

It is a further object of this invention to provide a technique for real-time analysis of average properties of the liquid-liquid dispersion system.

It is yet a further object of the invention to provide a system for monitoring a liquid-liquid dispersion system to provide data for reactor design, monitoring, and control.

According to the main principles of this invention, a representative sample stream of a dispersion is drawn through a glass capillary by developing a pressure difference across the tube. For this objective a vacuum can be employed. As drops of the dispersion pass through the capillary, they are transformed to generally cylindrical slugs of equivalent volume. An optical system is designed to measure drop size by difference of light refraction between the two phases and drop concentration by light absorbence of the solute in the drop. A light source of appropriate wave length is used to measure the drop size and its concentration simultaneously. A He-Ne laser of 632.6 nm wavelength and 10 mW power can be favorably employed, because the wave length is near the maximum absorptivity of the organic cobalt complex ($\epsilon = 168.5$ l/mol.cm at 626 nm) employed in this example. The laser beam is split into two beams to follow separate paths, by using a beam splitter and a plane mirror. The two light paths pass directly through the center of the capillary tube at a predetermined known separation, here precisely 10 cm apart. This precision adjustment is accomplished e.g. by the use of fine optical micropositioners mounted on an optical bench. The emergent beams from the capillary bore are then collected by respective ten power microscope objective lenses, the light being passed through pinholes to exclude stray light. The collected light is brought to focus on the sensitive area of respective photodiodes or phototransistors. The laser beam achieves a good contrast between the light signals given by the organic phase and the aqueous phase due to the difference in refractive index as between the two phases.

The measurement of passage time of the slug at one detector and its travel time between the two detectors can be used to calibrate the velocity and the drop diameter. The photodetectors provide pulse signal outputs in which the pulse width is a measure of the drop diameter. The pulse height is proportional to the molar absorptivity of a chemical species in the drop which could be, for example, (a) formed by chemical reaction in the drop, (b) formed by chemical reaction in the aqueous phase and transported into the drop, or (c) by being transported into the drop from the aqueous phase due to physical mass transfer, e.g., a cobalt complex in the organic phase. The pulse height can be related to the cobalt complex concentration through an appropriate calibration curve which accounts for both light refraction and absorbence.

The photodetector outputs can be digitized and stored as a data stream in a conventional magnetic storage device, e.g. a hard disc of a small or personal computer. These data can be analyzed in real time to produce average drop size data and average drop concentration data, and can produce a bivariate drop-size/concentration data analysis so that the progress of an ongoing reaction can be monitored and adjusted as need be.

The above and many other objects, features, and advantages of this invention will be more fully appreciated from the ensuing description of a preferred embodiment, which should be read in connection with the accompanying Drawing.

DETAILED DESCRIPTION OF THE PREFERRED EMBODIMENT

Figures 1, 1A, 1B:
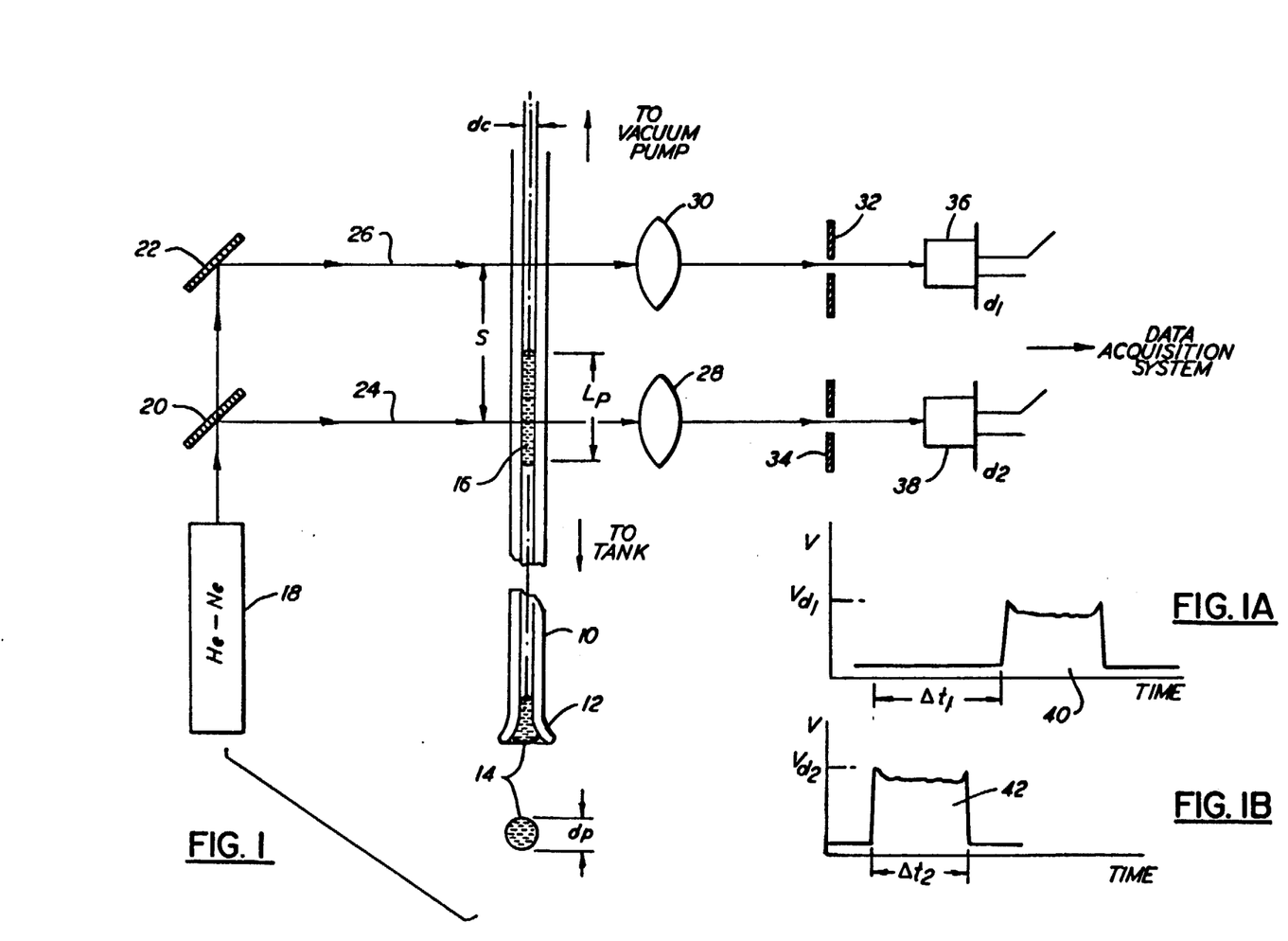
FIG. 1 is schematic view of salient elements of one embodiment of the invention.
FIG. 1A and 1B are voltage output waveforms of photodetectors employed in this embodiment.

With reference initially to FIG. 1 of the Drawing, an embodiment of the laser capillary spectrophotometric apparatus of this invention employs a glass capillary tube 10 that has a capillary bore with a diameter $d_c$, and a conical entrance 12 for receiving droplets 14 of the dispersed phase of a liquid-liquid dispersion. The droplets 14, which have a free diameter $d_p$, are deformed into cylindrical slugs 16, with a diameter that is the diameter $d_c$ of the capillary bore, and with a length $L_p$. The droplet 14 has the same volume before and after entering the capillary tube 10, so the length $L_p$ is directly proportional to drop volume.

An optical arrangement measures drop size by the difference in light refractive index between the two phases, and measures concentration in each droplet by light absorbence at or near a characteristic wavelength band or line for the solute in the droplet. An appropriate light source is employed to determine the drop size and concentration simultaneously.

A He-Ne laser 18, with a wavelength of 632.6 nm and a power of 10 mw is used in this example, because the wavelength is near an absorbence maximum of 626 nm for an organic cobalt complex employed in the example.

The laser produces a beam which passes through a beam splitter 20 to a plane mirror 22, and these two elements split the beam along two parallel paths 24,26 that pass through the center of the capillary tube 10 at locations that are a precise distance S apart, here, 10.00 cm. Precision adjustment is accomplished with fine micropositioners mounted on an optical bench. The beams that emerge from the capillary tube 10 then are collected by objective lenses 28,30 and the collected light passes through pin holes 32,34 to exclude stray light and comes to focus on sensitive areas of respective photodiodes 36,38. The laser beam gives good contrast between light levels passing through the organic phase and the aqueous phase due to the differing refractive indexes of the two phases.

The diodes 36 and 38 produce respective pulse signals 40,42 representing the intensity of light, at the wavelength of interest, that falls on each diode as the slug 16 proceeds across each of the light paths 24 and 26. There is a low finite base line signal through the aqueous phase and a peak through the organic phase, as shown in FIGS. 1A and 1B. Each pulse signal 40,42 has a respective amplitude $Vd_1$ or $Vd_2$ that is related to the absorptivity of the organic phase for the particular wavelength.

For each slug 16, there is a travel time $\Delta t_1$ between the two photodiodes 36 and 38, and a passage time $\Delta t_2$ of the slug 16 at either photodiode. The velocity V of the slug 16 through the capillary 10 is simply $$V = S \div \Delta t_1$$

The length of the slug $L_p$ moving at that velocity V is $$L_p = V \times \Delta t_2.$$

With the assumption that the slug 16 has a cylindrical shape and a diameter equal to the capillary diameter $d_c$, the droplet free diameter $d_p$ is proportional to the cube root of the slug length $L_p$, namely $$d_p = \left(\frac{3}{2} d_c^2 L_p\right)^{\frac{1}{3}}$$

or $$d_p = \left(\frac{3}{2} d_c^2 S \frac{\Delta t_2}{\Delta t_1}\right)^{\frac{1}{3}}$$

This computation can be carried out in real time or near real time on a suitably programmed small computer or dedicated information processor.

The pulse height $Vd_1$ or $Vd_2$ is proportional to the molar absorptivity of the cobalt complex in the organic phase. The pulse height can be related to the cobalt complex concentration through an appropriate calibration curve which accounts for both light refraction and absorbence.

Figures 2, 2A:
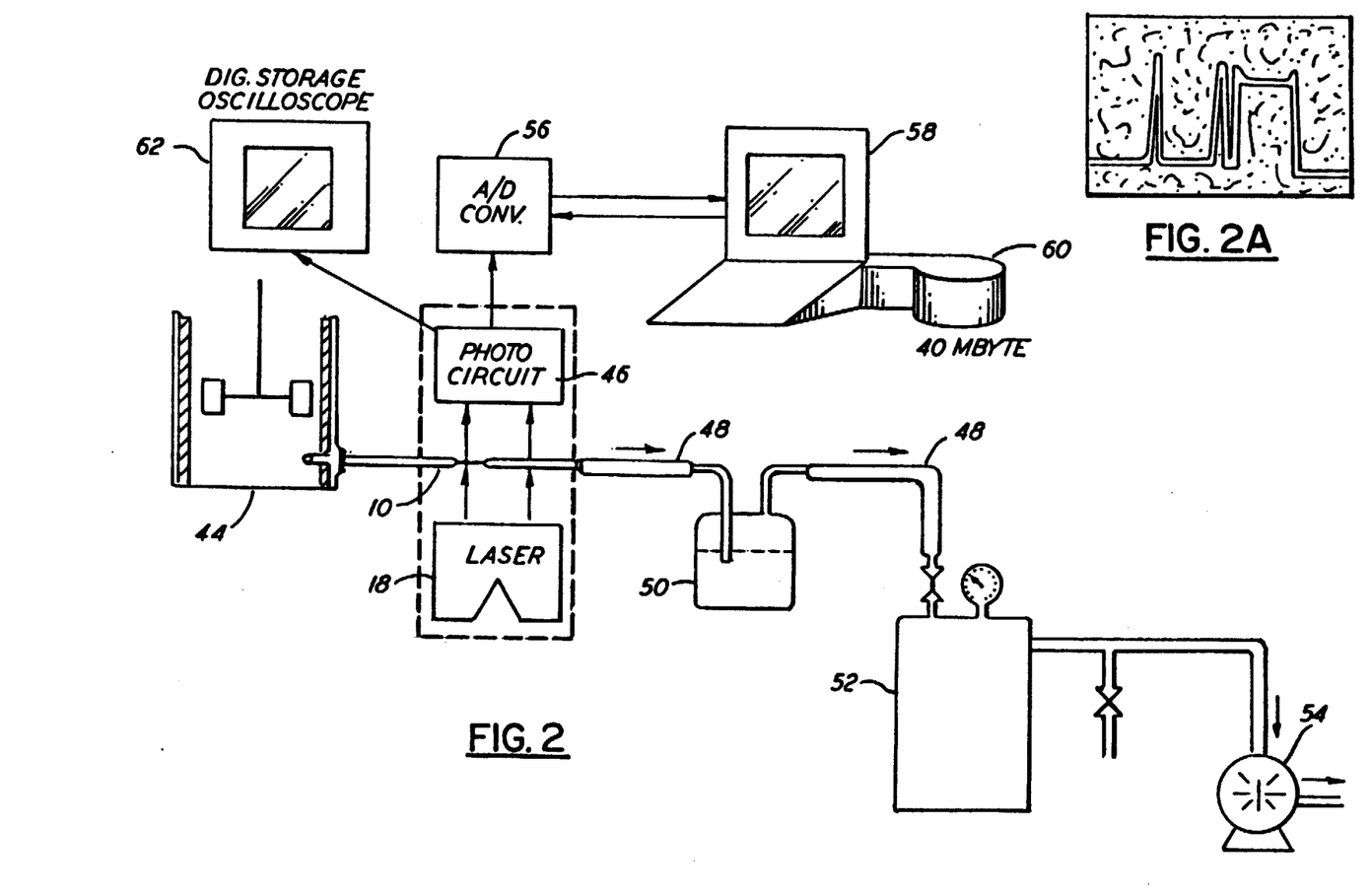
FIG. 2 is a system schematic of this embodiment of the invention.
FIG. 2A is a chart of a pulse waveform constituted by the detected amplitude from the optical system of the preferred embodiment.

A more detailed system diagram appears in FIG. 2. An inlet end of the capillary tube 10 projects into a reactor cell or vessel 44, where it is immersed to a sampling point which contains the agitated liquid-liquid dispersion. Here, the tube 10 is a precision-bore capillary with a heavy wall weight, 5.0 mm outside diameter, and 0.005 mm tolerance bores of 0.10, 0.15, or 0.20 mm, for example. The capillary tube 10 has a funnel or entrance 12 with an angle of 45° to 60°.

The capillary tube 10 passes through an optical system that comprises the He-Ne laser 18 and a photodetector circuit 46, which includes the diodes 36,38. A suction end of the tube 10 is connected by Viton tubing 48 to a liquid trap, and thence through a vacuum storage jar 52 to a vacuum pump 54 which can be of any suitable design. The vacuum system, comprised of these elements, provides the drive for drawing the dispersion at a suitable velocity through the capillary tube 10. Outputs of the diodes 36,38 are fed to inputs of a digitizer or A/D converter 56 which provides the output levels from the diodes as a stream of sample data to a suitably programmed small computer 58, and the data stream can be stored on a memory device, such as a 40-Megabyte hard disk drive 60 associated with the computer 58. In one suitable application an IBM PC-XT or equivalent has been employed. The photodetector circuit 46 also provides the pulse signals 40,42 to a digital storage oscilloscope 62, which produces a display of the sequence of pulses as shown, e.g., in FIG. 2A. The computer 58 is programmed to synchronize the signals from the photodiodes by finding three consecutive matching pulses from each of the photodiodes 36,38. The computer then calculates the drop velocity V, based on the sampling rate and the distance S. Then using this drop velocity V and a previously obtained drop concentration calibration curve, the drop sizes and concentration for each detected drop are calculated, and the data can be further processed and/or displayed in any of a variety of statistical forms.

Figure 3:
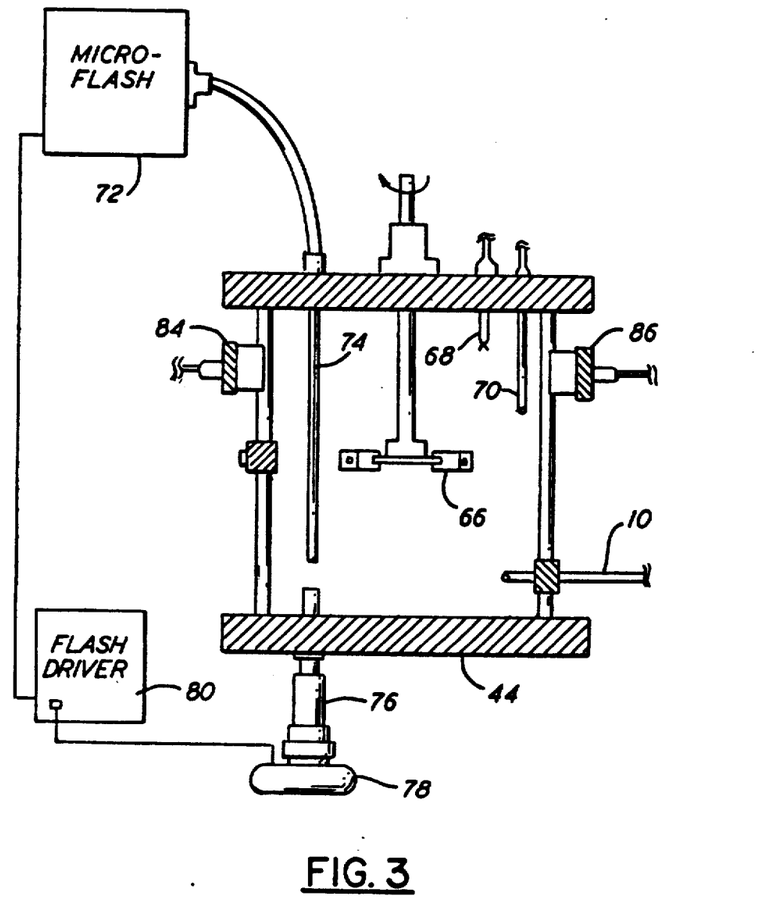
FIG. 3 is a schematic view showing a laser capillary spectrophotometric system of this invention coupled to a reactor tank.

A test set-up here is shown in FIG. 3, where a laser capillary spectrophotometric (LCS) system is adapted to an 0.75-liter baffled, stirred tank serving as the reactor 44. The tank has a flat-bladed Rushton-type rotary stirrer 66. In order to verify the LCS technique, measurement devices for drop size and average drop concentration are also installed.

A coalescor 68 is employed for sampling the dispersion to measure average distribution of the organic phase. The coalescor 68 comprises a brush or cluster of hydrophobic needles attached to the end of a Teflon tubing, and is immersed into the dispersion in the reactor. A mild vacuum is applied to enhance separation speed. Then the concentration of the cobalt complex (or other chemical solute) is measured.

A thermocouple 70 is also immersed into the liquid-liquid dispersion.

A photomicrographic technique is carried out to determine drop size distribution employing a system shown on the left-hand side of FIG. 3. A microflash 72 is coupled to an optical fiber 74 that extends into the dispersion in the vessel 44. A microscope 76 faces towards the distal end of the fiber 74 and focuses an image of the drops onto a camera 78. A flash drive 80 synchronized by the camera 78 powers the microflash 72.

The reactor 44 is also adapted to measure dispersed phase volumetric fraction employing the technique of Tavlarides and Bonnet U.S. Pat No. 4,726,221. Ultrasonic transducers 84 and 86 are disposed on the vessel wall for carrying out this measurement.

Figure 4:
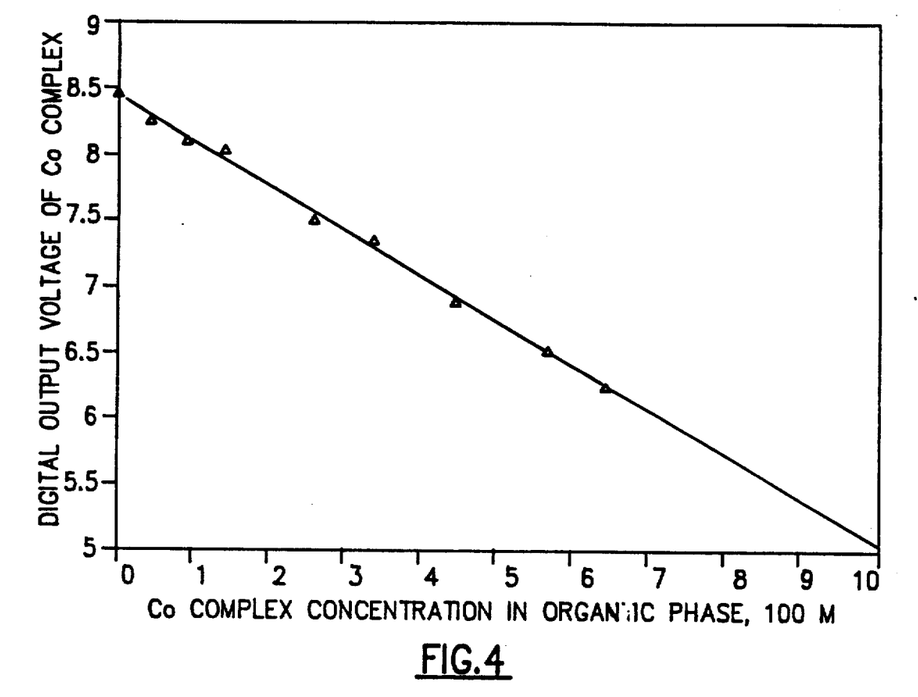
FIG. 4 is a calibration curve for concentration of a particular chemical species.

In operation, the reactor vessel 44 is charged with feed solution at the desired ratio the stirrer 66 is actuated, and the vacuum pump 54 is started. A continuous sample of the dispersion is withdrawn through the capillary 10, and the optical system is adjusted to obtain a series of rectangular pulses. Then, steady state operation data acquisition is commenced. Simultaneously, the dispersed phase is sampled with the coalescor 68 and photomicrographs of the droplets are taken. The calibration of drop concentration is carried out after draining the dispersion from the reactor 44. Here, approximately 0.5 μl of cobalt complex of known concentration in toluene is injected into the capillary entrance through a Viton plug hole using a Chempette digital micropipetter. The characteristic output digital data of the organic sample corresponds to a known cobalt concentration measured by atomic adsorption spectroscopy. Repeating this procedure with various cobalt concentration provides calibration curves shown, e.g., in FIG. 4. For calculation of drop concentration from the stored data, only the central flat part of the pulse is considered for the average output signal.

Figure 5:
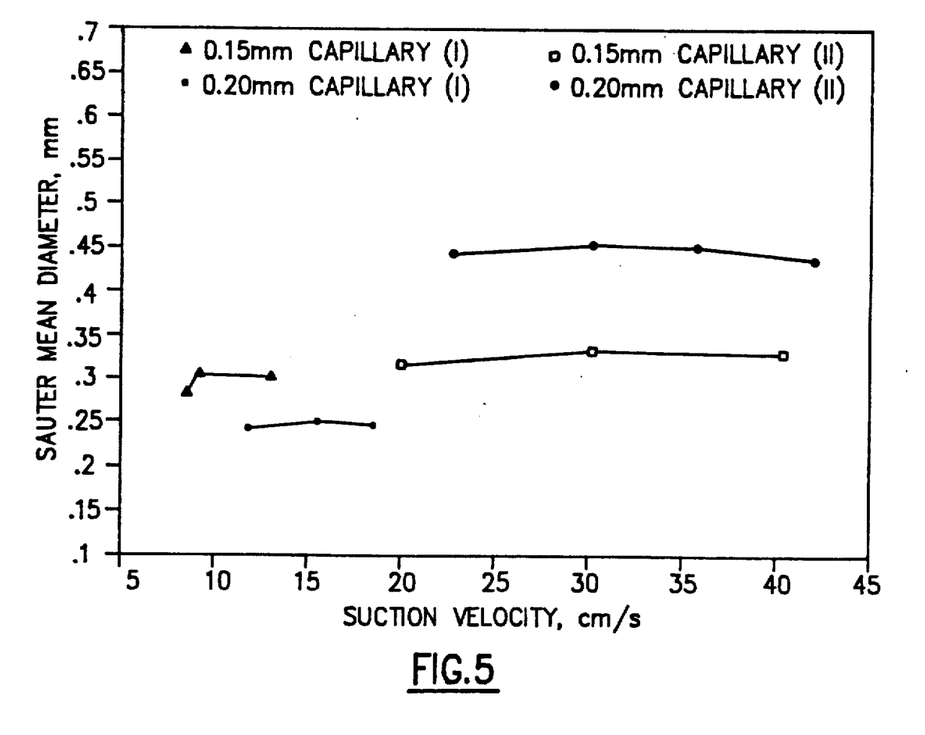
FIG. 5 is a chart showing the influence of suction velocity on drop effective diameter for several selected capillary tube diameters.
Figure 6:
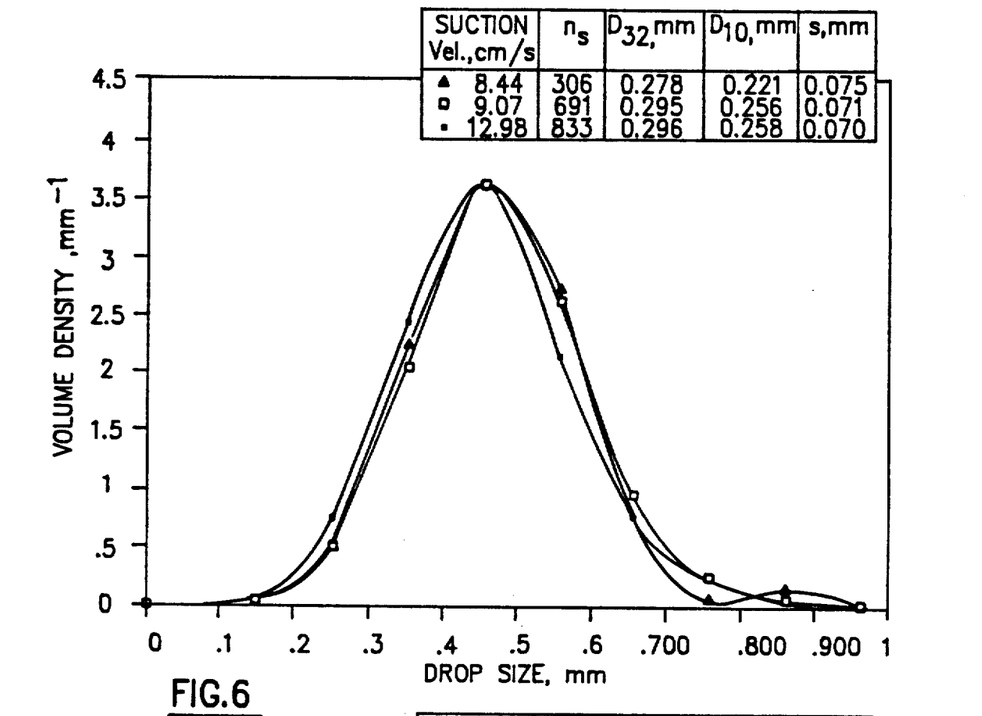
FIG. 6, 7, and 8 are charts showing experimental drop size distributions for two liquid dispersion systems, using various combinations of capillary tube and suction velocity.
Figure 7:
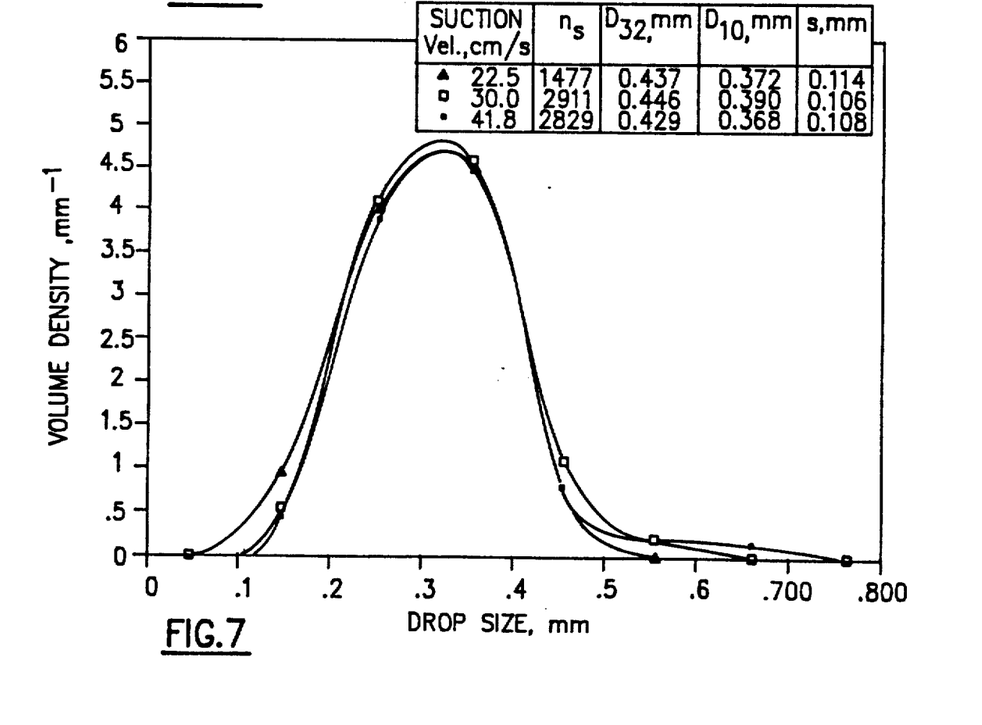

Three different sizes of capillaries ($d_c = 0.10, 0.15$ and $0.20$ mm) were employed in tests of the LCS technique. The very small diameter capillary ($d_c = 0.10$ mm) experienced limited capillary suction velocity (maximum 10 cm/s). Thus the results from the other two sizes are discussed here. For drop size measurement, toluene-water ($\sigma = 28 \pm 1$ dynes/cm) and 0.01M cobalt (2) nitrate-acetate buffer/1M D2EHPA-toluene ($\sigma = 13 \pm 0.5$ dynes/cm) systems were studied. For drop concentration measurements, the latter reactive system was studied. The stoichiometric equation of this reaction system is as follows:

$$Co^{2+} + 2\overline{(HR)_2} \rightleftharpoons \overline{CoR_2(HR)_2} + 2H^+,$$

where an overbar represents the species existing in the organic phase, and $\overline{(HR)_2}$ represents the dimeric form of D2EHPA. Measurement of Drop Size Drop size in liquid-liquid dispersions were measured for different suction velocities by changing vacuum suction pressure. The influence of suction velocity on Sauter mean diameters for two difference capillary sizes is shown in the chart of FIG. 5. The Sauter mean diameter is substantially constant above a suction velocity of 9 cm/sec for capillary diameter $d_c = 0.15$ mm and 20 cm/sec for capillary diameter $d_c = 0.20$ mm. Capillary suction velocity also does not influence the drop size distribution above these suction velocities as shown in the chart of FIG. 6 (here, $d_c = 0.15$ mm) and FIG. 7 (here, $d_c = 0.20$ mm). Thus, throughout these experiments, the LCS system is operated at suction velocities above 9 cm/sec for the 0.15 mm capillary and above 20 cm/sec for the 0.20 mm capillary.

Figure 8:
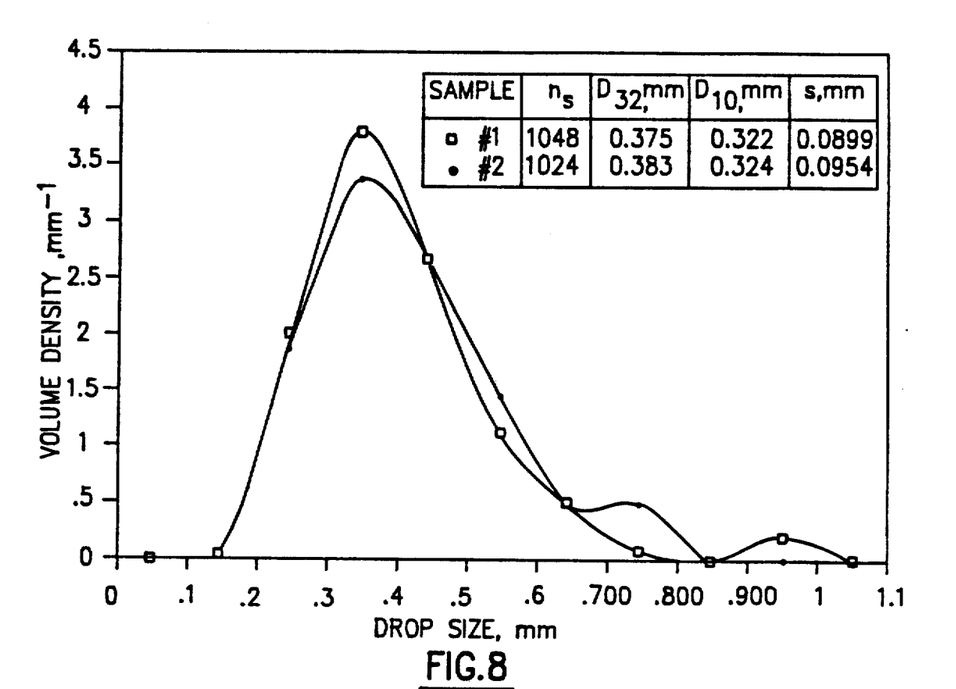

The accuracy of any measurement technique is determined by the reproducibility of the results obtained. FIG. 7 is one example of reproducibility of the LCS technique for drop size distribution in a toluene-water system. Even though suction velocities are changed from 22.5 to 41.8 cm/s, the drop size distributions do not change and almost superimpose each other. Further, the standard deviations of the distributions are close. FIG. 8 shows comparison of drop size distributions for two successive samples during continuous reactor operation with feed solutions of 0.01M cobalt nitrate and 1.0M D2EHPA in toluene at operation conditions of volumetric holdup $\phi = 0.077$, sampling time $\tau = 45s$, and stirrer speed of 300 rpm. In these figures, there is clearly good agreement between the two distributions.

The good reproducibility of the LCS technique can be attributed to several factors. First, isokinetic sampling of the dispersion is carried out by the LCS technique since the Sauter mean diameters and drop size distributions are independent of capillary suction velocity and entrance angle of the capillary. Two types of capillary entrance angle (45°, 60°) were tested for drop size measurement. The results for both types of capillaries also give close values of drop size (Sauter mean diameter and drop size distribution). Second, the accuracy is improved due to large sample size of drops per experiment (1000–3000). Third, an assumption that the film between the capillary wall and the drop is negligible, in volume calculations, is valid for these systems. Fourth, the rounding-off error from neglecting small droplets ($d < 0.05$ mm) does not affect drop size distribution on a volume basis, due to the small relative volume of these very small droplets.

Figure 9:
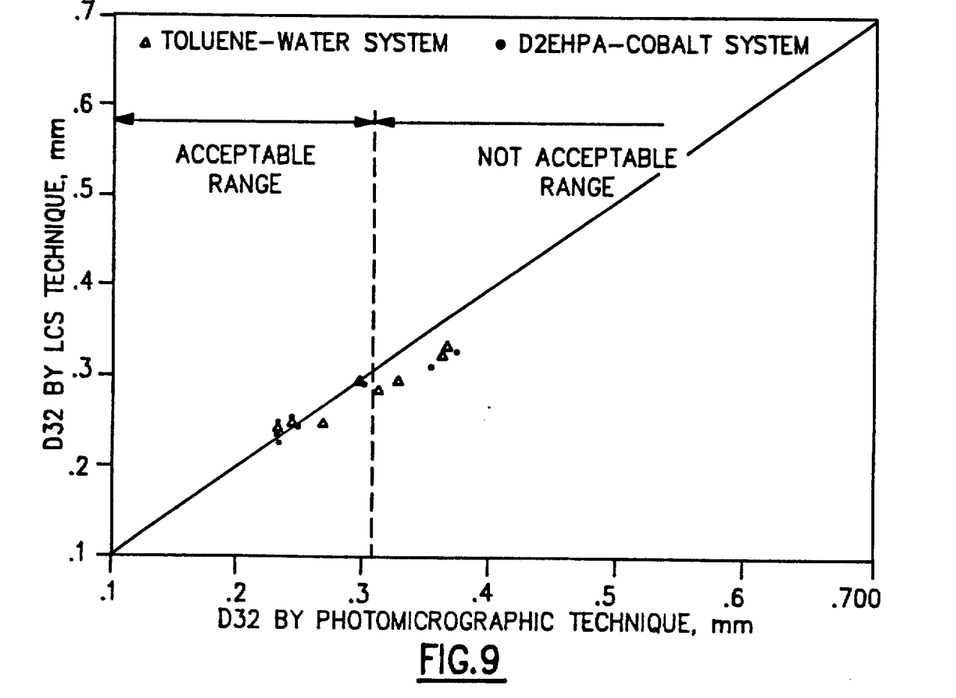
FIGS. 9 and 10 are charts showing agreement of drop size diameter analysis of the technique of this invention with a prior-art photomicrographic technique.
Figure 10:
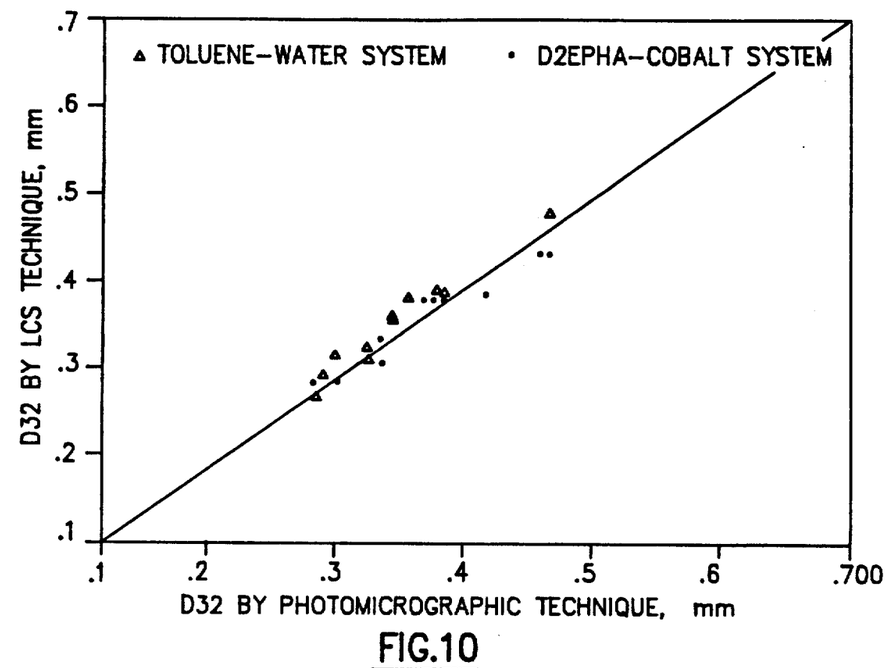

Drop size measurements by the photomicrographic method for the toluene-water system and the cobalt nitrate - D2EHPA in toluene systems were taken for comparisons with measurements from the LCS technique. Comparisons summarized in the following table show that the standard measurement error (below 4.97%) of the Sauter mean diameter determined by the LCS techniques is smaller than the error by the photomicrographic method. An error analysis shows the greatest uncertainty of drop size measurement by the LCS techniques comes from lack of precision in controlling the operating conditions of the reactor, such as flow rates, phase fraction and RPM. For example, when an 0.30 mm diameter drop passes through the 0.2 mm capillary at 30 cm/sec and data acquisition is operated at a 10 kHz sampling rate, the uncertainty of drop size measurement calculated by the method of propagation of errors, incorporating the errors of measurement in $d_c$, $\Delta t_2$ and V is only 2.61%. Comparison of the two techniques for measurements of Sauter mean diameter (D32) is shown in FIG. 9 for an 0.1.5 mm capillary and in FIG. 10 for an 0.20 mm capillary. In FIG. 9 the LCS techniques are in good agreement with the photomicrographic techniques below Sauter mean diameter $D_{32}=0.30$ mm. Above a Sauter mean diameter $D_{32}$ of 0.30 mm (or $d_p=0.6$ mm), the LCS measurements gives significantly smaller values of $D_{32}$ than the values measured by the photomicrographic technique. This difference is attributed to the inability of the capillary to capture larger drops because of the limited capillary suction velocity (maximum is about 19 cm/sec for $d_c=0.15$ mm). This can preclude isokinetic sampling of the dispersion for this range of larger drop sizes. However, simply by using a larger capillary, e.g., the 0.2 mm capillary, the LCS system is in good agreement with the photomicrographic technique in the range of $D_{32}=0.26$ to 0.55 mm ($d_p=0.05$ to 1.0 mm), as shown in FIG. 10. Accordingly, the LCS technique can measure drop size accurately over a broad range, simply by selecting the proper capillary size consistent with the drop size range of interest.

MEASUREMENT OF DROP CONCENTRATION

Drop concentration measurements for cobalt complex were conducted with an 0.2 mm capillary to ensure isokinetic sampling and high sensitivity of concentration measurements. However, with this capillary, concentrations in drops below 0.2 mm diameter cannot be measured accurately since a triangular type output signal is produced instead of rectangular pulse signals. These output signals cannot be unambiguously related to the drop concentration. The approximate diameter of these drops can be estimated by measuring the duration time of the triangular signals above a threshold detection voltage.

Figure 11:
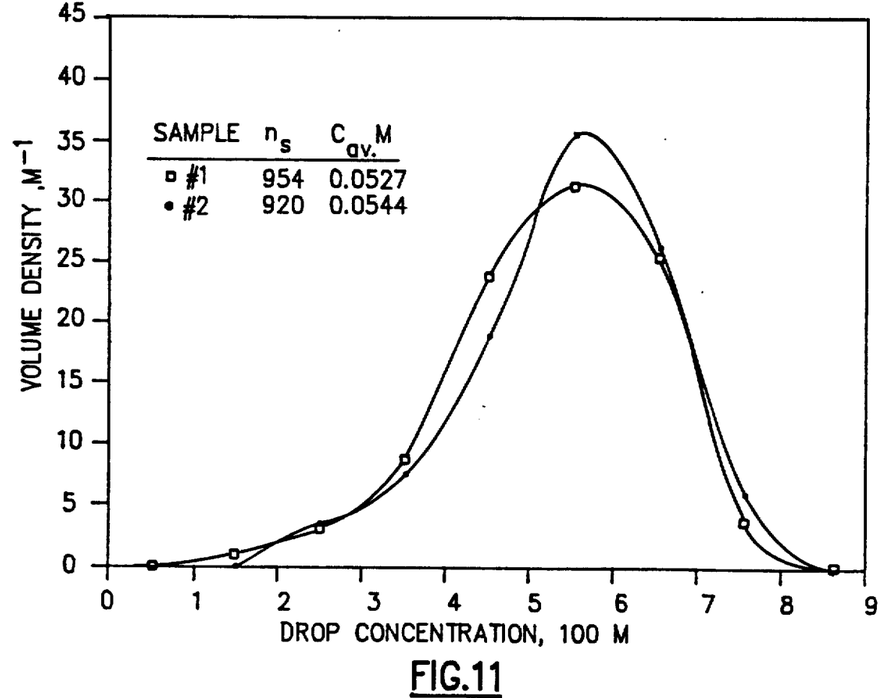
FIG. 11 is a chart showing drop concentration distribution for successive samples of a reactive flow system, using the technique of this invention.
Figure 12:
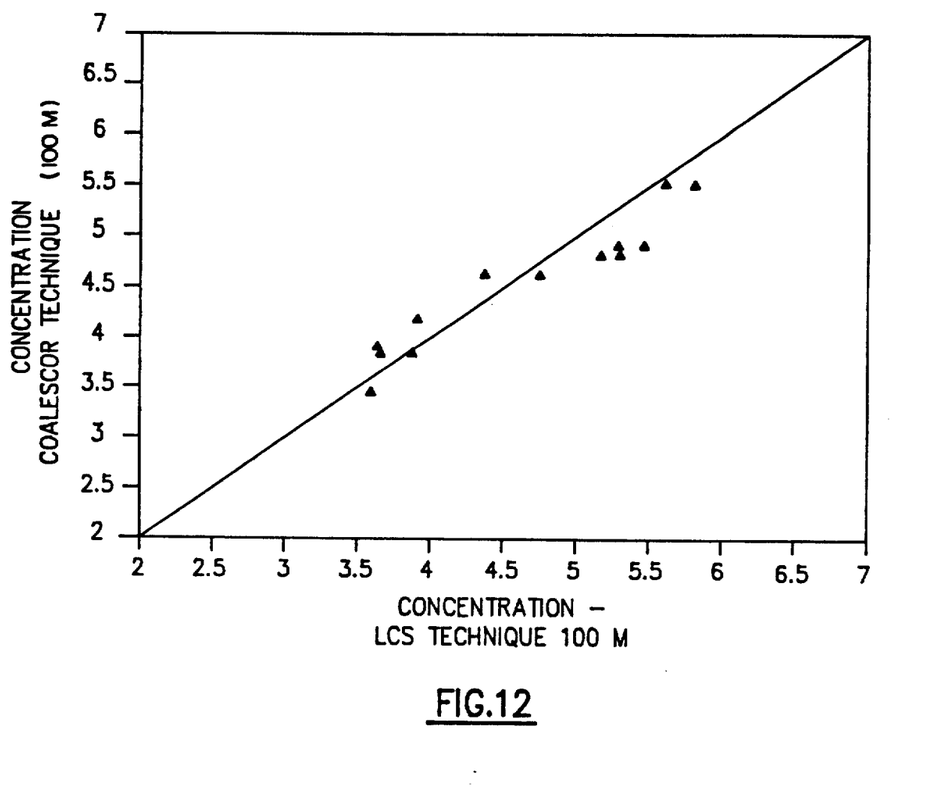
FIG. 12 is a chart showing agreement of concentration measurements employing the present invention with concentration measurements employing a prior-art coalescor technique.

FIG. 11 illustrates the reproducibility of the drop concentration distribution for two consecutive samples for the reactive flow systems with feed solutions of 0.01M cobalt nitrate (pH=4.0) - 1M D2EHPA-in-toluene system at holdup fraction $\phi=0.077$, residence time $\tau=45s$, and stirrer speed of 300 RPM, at steady state. Drop concentration distributions and average drop concentrations of the two successive samples are clearly in good agreement. Comparison of average drop concentration obtained by the LCS and the coalescor techniques are shown in FIG. 12. These results indicate that measurement values by the two techniques are in good agreement and within the measurement errors of both techniques. The measurement error of drop concentration by the LCS technique depends largely on the extent of light absorption by the cobalt complex. By the method of propagation of errors, the measurement error in drop concentration for a typical average concentration of 0.06M is 3.5% and for the minimum average concentration of 0.0350M, is 5.9%. For the lowest concentrations measured of 0.010M this error is 20%. This limitation may be improved upon by reducing noise signals coming from the optical and electronic systems.

Figure 13:
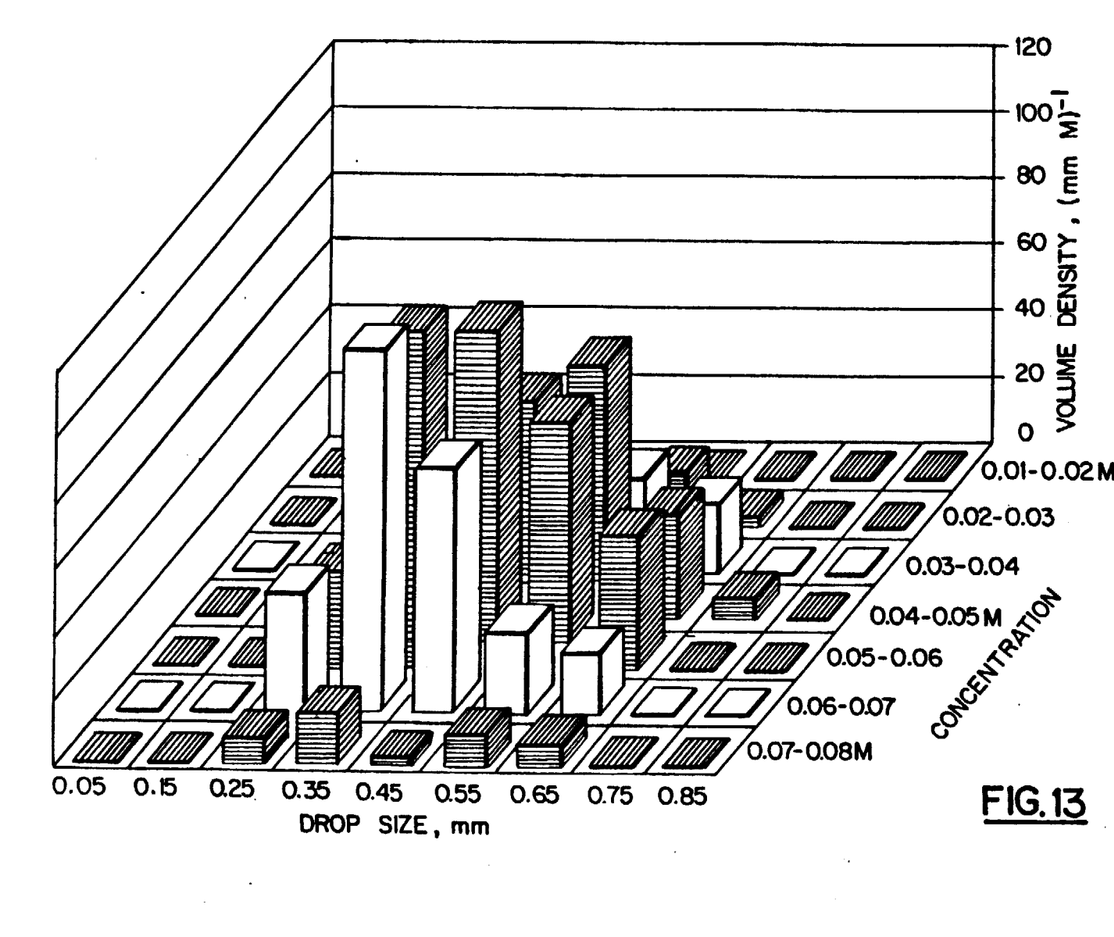
FIGS. 13 and 14 are charts of bivarite drop size and concentration distributions, produced employing the techniques of the present invention.
Figure 14:
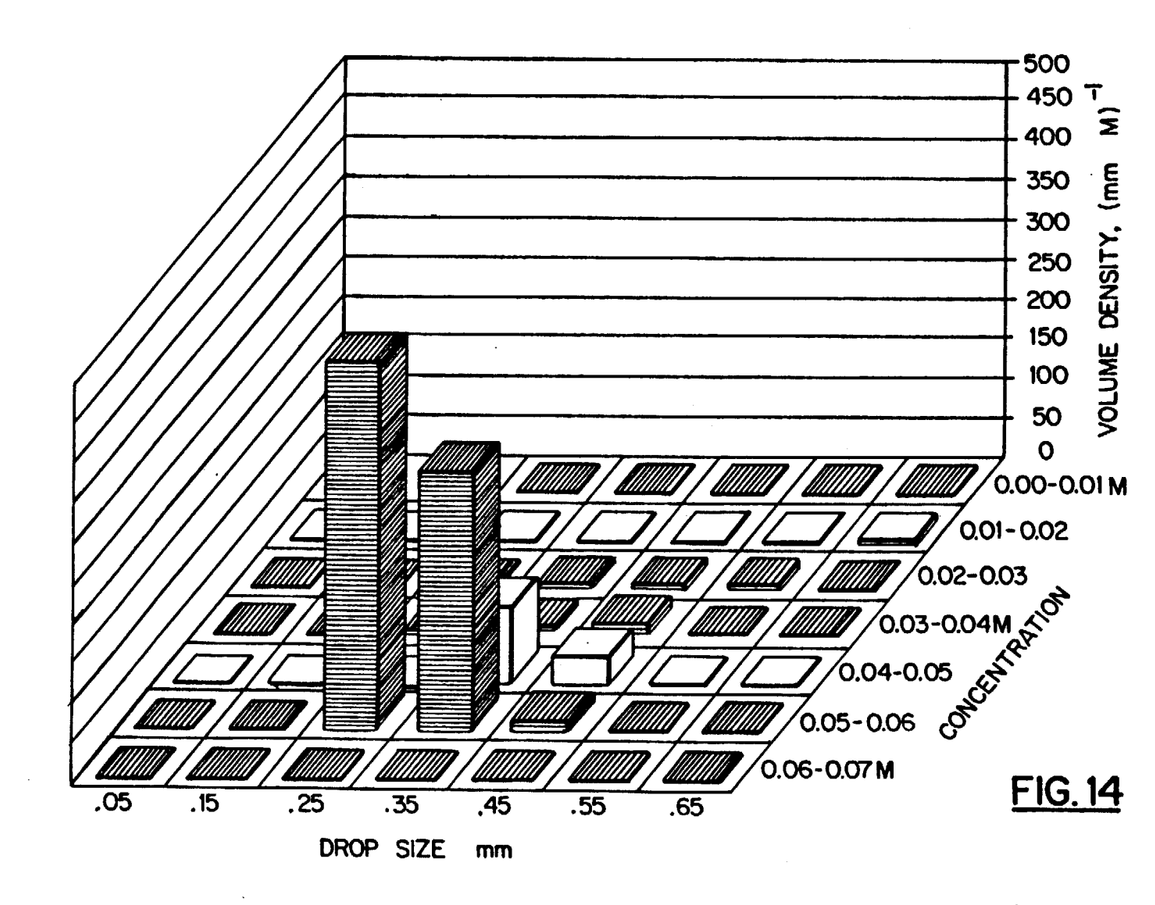

Bivariate drop size-concentration distributions for this system at the above feed conditions and at a steady state operation are shown in FIG. 13 for $\phi=0.077$, $\tau=45s$, and RPM=250 and in FIG. 14 for $\phi=0.10$, $\tau=120s$, and RPM=300. These bivariate distribution graphs can be calculated and displayed on the computer 58. FIG. 13 indicates that the drop concentrations are widely distributed (0.02M to 0.08M) over a broad range of drop sizes (0.2 mm to 0.8 mm) and perfect mixing of drop concentrations in the dispersed phase should not be assumed at these operation conditions. On the other hand, narrower distributions are observed at longer residence times and higher energy input: 0.03M to 0.06M for drop concentrations and 0.2 mm to 0.5 mm for drop diameters.

Conclusions

The LCS technique can measure drop size accurately and automatically over a broad range of drop sizes in liquid-liquid dispersion systems. This task is accomplished by the proper choice of the capillary size, depending on the drop size range to be measured. The drop size and the Sauter mean diameter are not influenced by the capillary suction velocities, as long as these are maintained above a certain level (e.g., 20 cm/s for a 0.2 mm capillary). The LCS technique shows good reproducibility for measurement of drop sizes and drop concentrations. Measured values of Sauter mean diameter and average drop concentration by the LCS technique are in good agreement with the photomicrographic and the coalescor techniques, respectively, and are within the measurement errors of these techniques. With the use of an 0.2 mm diameter capillary, the LCS technique generates bivariate drop size-concentration data of thousands of drops in the range of $d_p=0.05$ to $d_p=1.2$ mm ($D_{32}=0.25$ to 0.60 mm) within a few minutes. This is the first technique in which such data have been obtained for reactive liquid-liquid dispersion systems. Thus, the LCS technique can be a vital tool for the fundamental understanding of the effect of dispersed phase mixing on extraction efficiency and on selectivity for complex reactive liquid-liquid dispersion systems.

The LCS technique works well in the measurement of drop concentrations which have sufficient molar absorptivity. However, the technique can be improved for low concentration by reducing noise signals coming from the optical and electrical systems. The LCS technique can also be employed to measure multiple concentrations in the drop phase, i.e., by measuring absorption at multiple wavelengths. The utility of the technique to provide on line monitoring and control of the quality of processed liquid dispersions is clear.

While the technique of this invention has been explained with reference to a preferred embodiment, it should be understood that the invention is not limited to that precise embodiment. Rather, many modifications and variations would present themselves to persons skilled in the art without departing from the scope and spirit of this invention, as defined in the appended claims.

TABLE

MEASUREMENT ERRORS OF DROP SIZE OF PHOTOMICROGRAPHIC AND LCS TECHNIQUES

| | TECHNIQUES | | | | |
|---|---|---|---|---|---|
| | PHOTOMICRO-GRAPHIC TECHNIQUE | 0.15 CAPILLARY TECHNIQUE | | 0.20 MM CAPILLARY TECHNIQUE | |
| NUMBER OF EXPERIMENTS | 6 | 6 | 6 | 8 | 5 |
| DISPERSION SYSTEM | TOLUENE WATER | D2EHPA/ COBALT | TOLUENE WATER | D2EHPA COBALT | TOLUENE WATER |
| STIRRER SPEED RPM | 300 | 300 | 300 | 300 | 300 |
| $\phi$ | 0.10 | 0.077 | 0.10 | 0.01 | 0.15 |
| $\tau$ (Sec) | $\infty$ | $\infty$ | $\infty$ | 45 | $\infty$ |
| SAUTER MEAN DIAMETER (MM) | 0.303 | 0.238 | 0.291 | 0.411 | 0.344 |
| STANDARD ERROR FOR SAUTER MEAN DIAMETER | 0.0172 (5.68%) | 0.0108 (4.54%) | 0.008 (2.57%) | 0.006 (1.46%) | 0.017 (4.97%) |

What is claimed is:

1. Laser capillary spectrophotometric apparatus for rapid measurement of drop size and concentration in a liquid-liquid dispersion within a reactor vessel, the dispersion being formed of two immiscible liquids with mass transfer occurring across a boundary between the liquids with or without reactions occurring in either or both liquids; comprising a transparent capillary tube having a bore of a predetermined inner diameter, means at an intake end in communication with the dispersion in said reactor vessel, and means on an outlet end for drawing the dispersion through said capillary tube at a desired controlled rate;

a source of coherent light for producing first and second beams of coherent light at a predetermined known wavelength and directing same along respective first and second paths which pass across the bore of said transparent capillary tube at locations separated by a predetermined known distance;

first and second sensor means sensitive to light at said known wavelength and positioned along said first and second paths, respectively, for detecting the amplitudes of said light beams passing across said capillary tube, and generating first and second signals that represent the amplitude of the first and second light beams after passing across the capillary tube;

processor means receiving said first and second signals and producing in real time or near real time, for at least selected ones of drops in said dispersion, drop size data based on respective times of said first and second signals and concentration data based on the detected amplitude of one of said first and second signals, said processor means being operative for calculating the velocity of said dispersion through said capillary tube by finding the differences in time of production of pulses in said first and second signals and arithmetically operating on said differences in time and said predetermined distance, including matching at least three successive pulses from said first and second signals.

2. Laser capillary spectrophotometric apparatus according to claim 1, wherein said source of light comprises a laser generating light at said predetermined wavelength, and beam splitter means for splitting an output of said laser into said first and second beams.

3. Laser capillary spectrophotometric apparatus according to claim 2 wherein said predetermined wavelength is selected to be at or near a principal absorption wavelength of a chemical species in one of the liquids in said dispersion.

4. Laser capillary spectrophotometric apparatus according to claim 1 wherein said sensor means each include a photodiode producing an output voltage generally proportional to the amplitude of light incident upon it.

5. Laser capillary spectrophotometric apparatus according to claim 1 wherein said processor means includes data acquisition means for storing, for each of a multiplicity of drops, the size and concentration data.

6. A method of measuring, in real time or near real time, drop size and concentration in liquid-liquid dispersions within a reactor vessel, wherein the dispersion is formed of two immiscible liquids with mass transfer occurring across a boundary between the two liquids with or without reaction in either or both liquids, comprising the steps of continuously withdrawing a fraction of the dispersion within said reactor vessel and supplying same to a capillary tube having a bore of a predetermined inner diameter, and drawing the dispersion through the capillary tube;

transmitting a beam of coherent light of a predetermined wavelength across the bore of said capillary tube at each of the first and second locations along said tube which are separated by a predetermined known distance;

detecting amplitude of said light beam through the capillary tube at each of said first and second locations, and providing first and second signals that represent amplitudes of the light beam after passing through the capillary tube; and on the basis of relative timing of said first and second signals, producing drop size data for at least selected drops in said dispersion, and on the basis of the detected amplitudes of said light beam passing across said capillary tube at said predetermined wavelength, producing concentration data for each of said selected drops, including calculating velocity of said dispersion through said capillary tube by finding the difference in times of production of pulses in said first and second signals and arithmetically operating on said difference in time and said predetermined distance, including matching at least three successive pulses from said first and second signals.

7. Method of measuring drop size and concentration according to claim 6, further comprising digitizing said first and second signals and storing the digitized signals sequentially in a memory device.

8. Method of measuring drop size and concentration according to claim 6 further comprising producing from the computed drop size data and concentration data for each of said drops a bivariate plot of drop size, concentration, and number of drops, and displaying said plot.

9. A method of measuring in real time or near real time the drop size in a reactive liquid-liquid dispersion within a reactor vessel, wherein said dispersion is formed of two immiscible liquids with mass transfer occurring across a boundary between the two liquids with or without reactions occurring in either or both liquids, comprising the steps of continuously withdrawing a fraction of the dispersion within said reactor vessel and supplying same to a capillary tube having a bore of a predetermined diameter, and drawing the dispersions through the capillary tube;
   transmitting a beam of coherent light across the bore of said capillary tube at each of first and second locations along said tube which are separated by a predetermined known distance;
   detecting amplitudes of said light beam across the capillary tube at each of said first and second locations, and providing first and second signals that represent amplitudes of the light beam after passing across the capillary tube;
   calculating velocity of said dispersion through said capillary tube by finding the difference in times of production of pulses in said first and second signals and arithmetically operating on said difference in time and said predetermined distance, including matching at least three successive pulses from said first and second signals; and
   on the basis of said velocity and the width of said first and second signals, producing drop size data for at least selected drops in said dispersion.

10. Method of measuring drop size according to claim 9, further comprising producing average drop size data for a group of said selected drops.

11. A method of measuring in real time or near real time drop concentration in a liquid-liquid dispersion within a reactor vessel, wherein said dispersion is formed of two immiscible liquids with mass transfer occurring across a boundary between the two liquids with or without reactions occurring in either or both liquids comprising the steps of
   continuously withdrawing a fraction of the dispersion within said reactor vessel and supplying same to a capillary tube having a bore of a predetermined diameter, and drawing the dispersion through the capillary tube at a selected rate;
   transmitting a beam of coherent light of a predetermined wavelength across the bore of a said capillary tube at a first location and a second location on said tube;
   detecting amplitude of said light beam across the capillary tube at said first location and said second location, and providing a respective first signal and second signal that represents the amplitude of the light beam after passing across the capillary tube;
   on the basis of the detected amplitude of said light beam passing through said capillary tube at said predetermined wavelength, producing concentration data for at least selected drops in said dispersion; and
   calculating velocity of said dispersion through said capillary tube by finding the difference in times of production of occurrences of said first and second signals and arithmetically operating on said differences in time and said predetermined distance, including matching at least three successive occurrences of said first and second signals.

12. Method of measuring drop concentration according to claim 11 further comprising providing average drop concentration data for a group of said selected drops.

* * * * *